(12) United States Patent
Roberts et al.

(10) Patent No.: US 6,821,722 B1
(45) Date of Patent: Nov. 23, 2004

(54) PROCESS FOR THE RAPID MEASUREMENT OF ENZYMATIC ACTIVITY IN A SOLID FEED SAMPLE

(75) Inventors: Neil Roberts, Stockport (GB); Janet Moores, Stockport (GB)

(73) Assignee: Adisseo France S.A.S., Antony (FR)

( * ) Notice: Subject to any disclaimer, the term of this patent is extended or adjusted under 35 U.S.C. 154(b) by 0 days.

(21) Appl. No.: 09/763,018

(22) PCT Filed: Aug. 16, 1999

(86) PCT No.: PCT/FR99/01990

§ 371 (c)(1),
(2), (4) Date: May 29, 2001

(87) PCT Pub. No.: WO00/11136

PCT Pub. Date: Mar. 2, 2000

(30) Foreign Application Priority Data

Aug. 19, 1998 (FR) .......................... 98 10533

(51) Int. Cl.$^7$ ................................ C12Q 1/00
(52) U.S. Cl. ........................ 435/4; 435/287.3
(58) Field of Search ................... 435/4, 287.3, 7.72

(56) References Cited

U.S. PATENT DOCUMENTS

| | | | | |
|---|---|---|---|---|
| 4,277,561 A | | 7/1981 | Monget et al. ............ | 435/14 |
| 6,001,587 A | * | 12/1999 | Turner et al. ............. | 435/41 |
| 6,143,543 A | * | 11/2000 | Michelsen et al. ......... | 435/196 |

FOREIGN PATENT DOCUMENTS

| | | |
|---|---|---|
| EP | 0223745 | 5/1987 |
| EP | 0381173 | 8/1990 |
| EP | 0493758 | 7/1992 |

OTHER PUBLICATIONS

Bio–Rad Life Science Research Products Catalogue, Price List S, 1993, p. 62.*
Megazyme (www.megazyme.com), endo–1,4–b–xylanase assay procedures, p. 6.*
Sabatier A. Method of Analysis for Feed Enzymes. J of Applied Poultry Research, 1996 5(4)408–413.*
Walsh G. Technical Note: Detection and Quantification of Supplemental Fungal Beta Glucanase Activity in Animal Feed. J Animal Science 1995 73(4)1074–1076.*
Burianova T. Assay of Very Low Cellulolytic Activity in Fodder Supplemented with Enzyme Preparation. Animal Feed Science and Technology 1991, 33(1–2)41–48.*
Heil, K. Assay of Enzyme Activity in Feeds. Zootecnica International 1997 20(3)40–43.*

* cited by examiner

Primary Examiner—Ralph Gitomer
(74) Attorney, Agent, or Firm—Connolly Bove Lodge & Hutz LLP

(57) ABSTRACT

The invention relates to a process for measuring the enzymatic activity of a solid feed sample wherein the process includes contacting the solid feed sample, a reagent for the enzyme whose activity it is desired to measure comprising a substrate specific for the enzyme linked to a chromophore, and a buffer for dissolving the enzyme, in a container fitted with a leak proof opening and closing system; shaking the container to distribute the chromophore in the liquid buffer; and then observing the coloration of the liquid phase, the coloration being proportional to the activity of the enzyme present in the sample.

10 Claims, 2 Drawing Sheets

Column of the device for measuring enzymatic activity

PROCESS FOR THE RAPID MEASUREMENT OF ENZYMATIC ACTIVITY IN A SOLID FEED SAMPLE

CROSS-REFERENCE TO RELATED APPLICATIONS (NOT APPLICABLE)

STATEMENT REGARDING FEDERALLY SPONSORED RESEARCH OR DEVELOPMENT (NOT APPLICABLE)

INCORPORATION-BY-REFERENCE OF MATERIAL SUBMITTED ON A COMPACT DISC (NOT APPLICABLE)

BACKGROUND OF THE INVENTION (1) Field of the Invention

The present invention relates to a device for the rapid measurement of an enzymatic activity in a solid feed, comprising (i) a container designed to contain the test sample, (ii) a reagent specific for the enzyme whose activity it is desired to measure, and (iii) a buffer for dissolving the enzyme.

The feed is preferably a solid feed which is not treated prior to the measurement.

(2) Description of Related Art

Feeds intended for husbandry animals are usually supplemented with enzymes whose role is mainly to improve the digestibility of the feed ration. These enzymes are usually sprayed in liquid from onto the feeds, in particular as described in patent EP 0,789,291. The enzymes can also be added in powder form to the feed.

Two problems thus arise, the first being to check the uniformity of distribution of the enzymes added to the feed, the second being to quickly and easily evaluate the activity of the enzyme(s) added to the feeds. These problems are raised in particular by feed manufactures and breeders wishing to check the quality of the feeds they want to give to their animals. Until now, the enzymatic activity could be measured in the laboratory, thus entailing constraints in terms of logistics and delays, these constraints being a real hindrance when an immediate result is needed.

BRIEF SUMMARY OF THE INVENTION

The present invention satisfies this problem by providing a device for measuring the enzymatic activity of any enzyme-enriched feed intended for animal feed. This device, whose measurement is based on a colorimetric reaction, allows both a qualitative measurement of the enzymatic activity of the test sample and a semi-quantitative measurement of this sample.

DETAILED DESCRIPTION OF THE INVENTION

Figure 1:
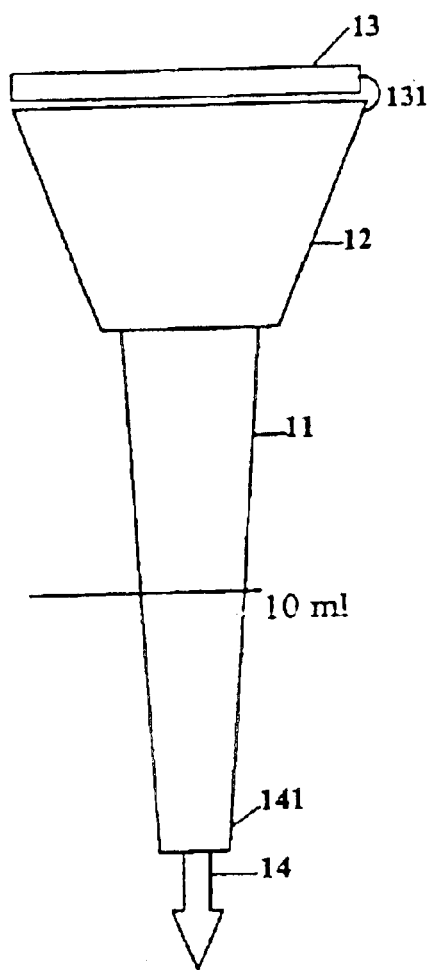
FIG. 1 shows a column for measuring enzymatic activity.

FIG. 1 represents one embodiment of the invention in the form of a device for measuring enzymatic activity, which is in the form of a column.

The description below can be read with regard to the figure mentioned above.

The device which is the subject of the present invention comprises a container designed to contain the test sample, a reagent specific for the enzyme whose activity it is desired to measure and a buffer for dissolving the said enzyme.

The container of this device can be, without any implied limitation, a column (FIG. 1) composed of a graduated narrow bottom part (11) and a wide funnel-shaped top part (12) for introducing various reagents into the column and for mixing them during stirring. The column can also be fitted with a leakproof opening and closure system (13) such as a stopper attached to the body of the column by means of a tab (131).

Figure 2:
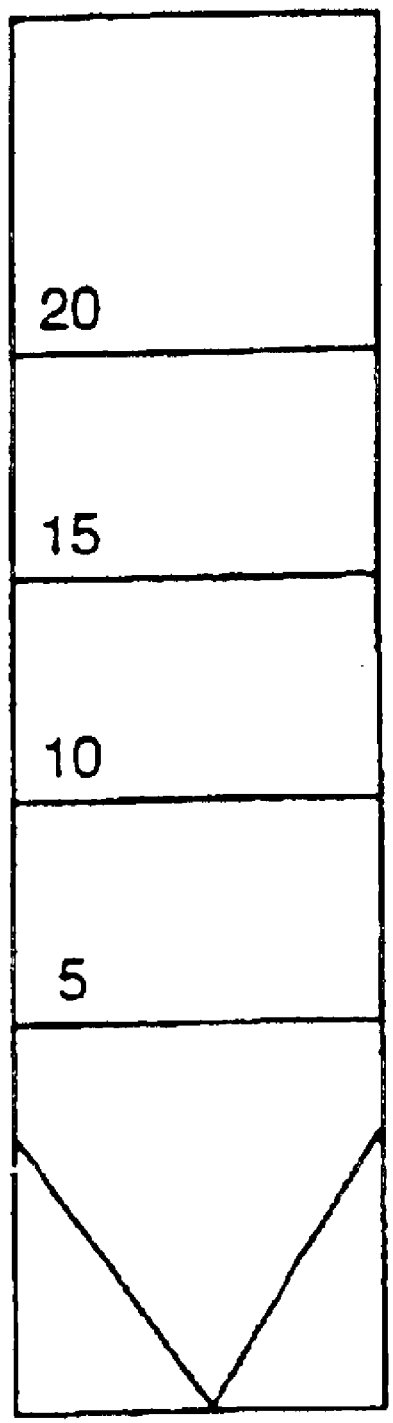
FIG. 2 shows a single use tube.

The container can also consist of a single-use tube (FIG. 2).

The container can be made of synthetic material such as a single-use plastic.

The container can preferably comprise a cleavable protuberance (14) at its base, allowing the liquid part of its contents to flow out. A constriction (141) retaining the solid morsels of feed is advantageously mounted on the protuberance.

Measurement of the enzymatic activity is based on the coloration reaction of the Azo method. The principle of the coloration reaction of the Azo method is based on the enzymatic hydrolysis of a characteristic substrate of an enzyme linked to a chromophore. The reaction produces soluble oligomers which turn the medium blue. The absorbence of the medium can be measured at 590 nm.

The reagent used in the device is the substrate of the reaction catalysed by the enzyme linked to a chromophore. Thus, the enzymatic hydrolysis reaction releases the chromophoric substrate.

The device also comprises a buffer for dissolving the enzymes which have been sprayed onto the feed, and for keeping the enzymes at their optimum pH.

Mention may be made, by way of example and without any restriction being implied, of the device for demonstrating the activity of xylanases.

To measure the activity of xylanases, the reagent used is "Oat spelt Xylan Remazol Brilliant Blue R" or "Xylazyme AX" (sold by the company Megazyme and consisting of oat or wheat araboxylane linked to a dye).

The buffer used is chosen from acetic acid/sodium acetate; glycine hydrochloride/glycine; aconitic acid/sodium hydroxide; formic acid/sodium formate buffers.

Mention may also be made of the device for demonstrating the activity of β-glucanases, which is also based on the coloration reaction of the Azo method.

Among the substrates which can be used, mention may be made of 1,3:1,4-β-D-glucan with Remazol Brilliant Blue R and Beta-Glucazyme sold by the company Megazyme and consisting of beta-glucan combined with azurine.

The buffer used is chosen from acetic acid/sodium acetate; glycine hydrochloride/glycine; aconitic acid/sodium hydroxide; formic acid/sodium formate buffers.

To measure the activity of cellulase, the substrate used is in the form of Cellazyme lozenges (sold by the company Megazyme). These lozenges consist of substrates based on cellulose and/or on cellulose and xyloglucans polymerized with an azurine dye.

In one preferred embodiment of the present invention, the reagent is in a solid form.

Advantageously, to facilitate the dissolution of the enzyme, a surfactant can be added to the substrate containing the chromophoric agent. This surfactant is chosen in particular from sodium lauryl sulphate and sodium dodecyl sulphate.

According to a better embodiment of the invention, the measurement is carried out in four steps:

- introduction into the container (1) of 10 ml of sample whose enzymatic activity it is desired to measure—for a solid sample, the container should be filled with solid up to the 10 ml graduation mark;
- introduction of the reagent in the form of a solid bead;
- introduction of the specific buffer up to the 20 ml graduation mark;
- after closing the column with the stopper, the column is shaken vigorously several times.

An additional step of separating the liquid phase and the solid phase (by centrifugation or filtration) can optionally be added, to recover the liquid phase and to measure the intensity of the coloration by spectrophotometry or simply by comparison with a colour scale.

The appearance of a blue coloration after a reaction time of 4 to 8 hours confirms the presence of active enzymes, the intensity of the coloration being proportional to the activity of the enzymes present in the sample.

Another advantage of the present invention is the ability to carry out a semi-quantitative measurement of the enzymatic activity. The coloured liquid phase in the column can be recovered by cutting off the cleavable protuberance from the column. The intensity of its coloration can then be compared with an OD calibration curve.

In addition to being fast, the measurement method is very simple and the device can be used anywhere without requiring special equipment. For example, a manufacturer or a breeder can carry out a control measurement as soon as the feed has been manufactured.

The present invention will be described more fully with the aid of the examples which follow, which should not be considered as limiting the invention.

EXAMPLES

Two series of tests were carried out on Rovabio xylan LC (mixture of xylanase and beta glucanase from *Penicillium funiculosum*) and on Rovabio xylanase TRLC (xylanase from *Trichoderma reesei*) whose xylanase activity is between 350 and 550 uAXC/ml. It is estimated that the treatment of spraying the liquid composition on the feeds leads to a level of 70 to 110 uAXC/kg of feed.

The buffer used is the acetate buffer for maintaining a pH of 4.7. The spraying can be carried out on the feed in pulverulent form or in granulated form.

| Sample | Activity (before adjustment) | Observation at 3 hours | O.D. at 590 nm at 4h30 | O.D. at 590 nm at 8h | Observation at 8h |
|---|---|---|---|---|---|
| xylanase TRLC on granules | 1336 | blue: +++ | >3.0 | >3.0 | blue: +++ |
| xylanase TRLC on granules | 886.7 | blue: + | 1.567 | 2.685 | blue: ++ |
| xylanase TRLC on granules | 1469.25 | blue: + | 1.429 | 2.652 | blue: ++ |
| xylanase powder before granulation | 631.4 | no coloration | 0.201 | 0.666 | blue: + |
| xylanase LC on granules | 1144 | blue: +++ | 2.309 | 2.376 | blue: +++ |
| xylanase LC on granules | 1386.7 | blue: + | 1.382 | 2.484 | blue: +++ |
| xylanase LC on granules | 1450.5 | blue: +++ | 2.872 | 2.85 | blue: +++ |
| xylanase LC on granules | 1330.5 | blue: ++ | 1.233 | 2.096 | blue: +++ |

What is claimed is:

1. Process for directly measuring the enzymatic activity of a solid feed sample in discrete form, comprising the following steps:
   a) contacting the solid feed sample, a reagent for an enzyme whose activity it is desired to measure comprising a substrate specific for the enzyme linked to a chromophore, and a buffer, in liquid form, for dissolving the enzyme, in a container that is fitted with a leak proof opening and closing system;
   b) shaking the container so that the chromophore is distributed in the liquid buffer to form a liquid phase, and
   c) observing the coloration of the liquid phase, the coloration being proportional to the activity of the enzyme originally present in the solid feed sample.

2. Process according to claim 1, wherein the solid feed sample is untreated.

3. Process according to claim 1, wherein the reagent is in solid or in liquid form.

4. Process according to claim 1, wherein the reagent is in the form of a solid bead.

5. Process according to claim 1, wherein the reagent is a substrate for the enzyme linked to a chromophore.

6. Process according to claim 1, wherein the buffer used to measure the activity of the enzyme is selected from the group consisting of acetic acid/sodium acetate, glycine hydrochloride/glycine, aconitic acid/sodium hydroxide and formic acid/sodium formate buffers.

7. Process according to claim 1, wherein the intensity of the coloration obtained is compared with a standard curve.

8. Process according to claim 1, wherein at step c) the liquid phase is separated from a solid phase, the liquid phase is recovered and the coloration is measured by comparison with a color scale.

9. Process according to claim 8, wherein the container comprises a cleavable protuberance at its base, which, upon cleavage, allows the liquid phase to flow out of the container.

10. Process according to claim 1, wherein the container is a single-use graduated column or tube.

* * * * *

UNITED STATES PATENT AND TRADEMARK OFFICE
CERTIFICATE OF CORRECTION

PATENT NO. : 6,821,722 B1
DATED : November 23, 2004
INVENTOR(S) : Neil Roberts et al.

It is certified that error appears in the above-identified patent and that said Letters Patent is hereby corrected as shown below:

Column 1,
Line 6, insert the following:
-- This application is a national stage filed under 371 of PCT/FR99/01990 filed August 16, 1999, which claims priority to France 98/10,533 filed August 19, 1998 --.

Signed and Sealed this

Sixteenth Day of August, 2005

JON W. DUDAS
*Director of the United States Patent and Trademark Office*